United States Patent
Tracey et al.

(10) Patent No.: US 9,005,615 B2
(45) Date of Patent: Apr. 14, 2015

(54) METHODS FOR TREATMENT OF INFLAMMATORY DISEASES

(75) Inventors: Kevin Tracey, Old Greenwich, CT (US); Sangeeta Chavan, Syosset, NY (US)

(73) Assignee: The Feinstein Institute For Medical Research, Manhassett, NY (US)

( * ) Notice: Subject to any disclaimer, the term of this patent is extended or adjusted under 35 U.S.C. 154(b) by 0 days.

(21) Appl. No.: 13/696,316

(22) PCT Filed: May 5, 2011

(86) PCT No.: PCT/US2011/000785
§ 371 (c)(1),
(2), (4) Date: Nov. 29, 2012

(87) PCT Pub. No.: WO2011/139368
PCT Pub. Date: Nov. 10, 2011

(65) Prior Publication Data
US 2013/0071389 A1    Mar. 21, 2013

Related U.S. Application Data

(60) Provisional application No. 61/343,966, filed on May 6, 2010.

(51) Int. Cl.
*A61K 39/395* (2006.01)
*C07K 16/22* (2006.01)
*C07K 16/38* (2006.01)
*A61K 39/00* (2006.01)

(52) U.S. Cl.
CPC ..... *A61K 39/39533* (2013.01); *A61K 2039/505* (2013.01); *C07K 16/22* (2013.01); *C07K 2317/76* (2013.01)

(58) Field of Classification Search
None
See application file for complete search history.

(56) References Cited

PUBLICATIONS

Rheumatoid Arthritis, Stedman's online Medical Dictionary, 2013.*
Arteriosclerosis, Stedman's online Medical Dictionary, 2013.*
Gout, Stedman's online Medical Dictionary, 2013.*
Appendicitis, Stedman's online Medical Dictionary, 2013.*
Hodgkin's diseases, Stedman's online Medical Dictionary, 2013.*
Adult Respiratory Distress Syndrome, Stedman's online Medical Dictionary, 2013.*
Sanagi et al, Neuroscience Letters 2005, vol. 380, pp. 105-110.*
Yamagishi et al, Current Pharmaceutical Design, 2009, vol. 15, pp. 1027-1033.*
Yamagishi et al., Current Pharm des, 2014; 2D(14):2377-238.*
Jenkins et al. Diabetes Res. Clinical Practice. 2008, Oct. 82(1): eS-e7.*
Jenkins et al, (Diabetes Medicine, vol. 24, 2007, pp. 1345-1351.*
Wiercinska-Drapalo et al., Regulatory Peptides, 2007, vol. 140, pp. 1-4.*
Tahara et al. (Atherosclerosis; 2011, vol. 219, pp. 311-315).*
PCT International Search Report dated Oct. 31, 2011 in connection with PCT International Patent Application No. PCT/US2011/00785, 6 pages.
PCT Written Opinion of the International Searching Authority dated Oct. 31, 2011 in connection with PCT International Patent Application No. PCT/US2011/00785, 5 pages.
Crowe S et al., entitled "Pigment Epithelium-Derived Factor Contributes to Insulin Resistance in Obesity," Cell Metabolism, 10, 40-47, Jul. 8, 2009.
Agwunobi A O et al., entitled Insulin Resistance and Substrate Utilization in Human Endotoxemia, J Clin Endocrinol Metab, 85:3770-3778, 2000.
Dub E J, et al., entitled "Pigment Epithelium-Derived Factor Suppresses Ischemia-Induced Retinal Neovascularization and VEGF-Induced Migration and Growth," Investigative Ophthalmology & Visual Science, Mar. 2002, vol. 43, No. 3, 821-829.

* cited by examiner

*Primary Examiner* — Bridget E Bunner
*Assistant Examiner* — Fozia Hamud
(74) *Attorney, Agent, or Firm* — Amster, Rothstein & Ebenstein LLP

(57) ABSTRACT

The present invention provides methods of treating inflammatory diseases in a subject comprising administering to the subject a therapeutically effective amount of an agent that inhibits pigment epithelium-derived factor (PEDF) and methods of screening for agents that inhibit PEDF.

9 Claims, 22 Drawing Sheets

A

B

A

B

A

B

A

B

A

B

METHODS FOR TREATMENT OF INFLAMMATORY DISEASES

CROSS-REFERENCE TO RELATED APPLICATION

This application is a U.S. national stage entry under 35 U.S.C. §371 of PCT International Pat. application Ser. No. PCT/US2011/000785, filed May 5, 2011, which claims priority to U.S. Provisional Pat. application Ser. No. 61/343,966, filed May 6, 2010, the contents of which are incorporated herein by reference in their entirety.

FIELD OF THE INVENTION

The present invention relates generally to methods of treating inflammatory diseases.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

Inflammation is the complex biological response of vascular tissues to harmful stimuli, such as pathogens, damaged cells, or irritants. Inflammation is a protective attempt by the organism to remove the injurious stimuli as well as initiate the healing process for the tissue. Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue.

Chronic inflammation progressively shifts the cells types present at the site of inflammation and is characterized by simultaneous destruction and healing of the tissue from the inflammatory process. Chronic inflammation in various tissues underlies a large group of diseases that include such inflammatory conditions as autoimmune diseases, inflammatory bowel disease, rheumatoid arthritis, endotoxemia, cancer, sepsis, atherosclerosis, vasculitis, transplant rejection, asthma, ischaemic heart disease, obesity-related insulin resistance and diabetes.

Obesity is a major risk factor for conditions ranging from metabolic syndrome and type 2 diabetes mellitus to atherosclerosis. Low grade inflammation leading to insulin resistance is a central feature of the pathophysiology of most obesity-related disorders. Chronic inflammation in fat plays a crucial role in the development of obesity-related insulin resistance. Increasing adiposity leads to inflammation and recruitment of immune cells to adipose tissue. The adipocyte itself is integral to the development of obesity-induced inflammation.

The innate immune response is driven primarily by signaling molecules collectively referred to as cytokines, which are used by cells of the immune system to communicate the integrity of the body's barriers to the environment. Cytokines are normally produced by immune cells in response to pathogen-associated molecules (PAMPs) or damage-associated molecules (DAMPs), and activate other immune cells to increase the body's immune response. There are two main classes of clinically relevant cytokines: pro-inflammatory mediators that activate and amplify inflammation and anti-inflammatory mediators that impede and balance the inflammatory response. A predominant belief amongst immunologists is that an unrestrained pro-inflammatory mediator cascade causes disease [1-11]. The dysregulated sequence of pro-inflammatory cytokines leading to disease has been referred to as a "cytokine storm" [12] or "inflammatory cascade" [13], as one cytokine typically leads to the production of multiple other cytokines to reinforce and amplify the immune response.

Pro-inflammatory mediators can be further broken down into two subgroups: early mediators and late mediators [1, 2, 15, 16]. Early mediators (tumor-necrosis factor, interleukin-1, interleukin-6, etc.) are not sufficient therapeutic targets for re-establishing homeostatic balance because they are resolved within the time frame of a patient's travel to a clinic to receive medical attention [1, 9-11, 14, 15]. Conversely, late mediators can be therapeutically targeted as they occur later in the "inflammatory cascade," after a patient has realized that he or she has fallen ill.

The present invention provides a method for preventing or treating myriad diseases mediated by chronic inflammation.

SUMMARY OF THE INVENTION

The present invention provides a method of treating an inflammatory disease in a subject, the method comprising administering to the subject a therapeutically effective amount of an agent that inhibits pigment epithelium-derived factor (PEDF).

The present invention provides the use of a PEDF inhibitor that inhibits PEDF for the treatment of an inflammatory disease in a subject.

Also provided is a method of identifying an agent for treating an inflammatory disease in a subject, the method comprising determining whether or not the agent inhibits pigment epithelium-derived factor (PEDF), wherein an agent that inhibits PEDF is identified as a candidate agent for treating an inflammatory disease and an agent that does not inhibit PEDF is not identified as a candidate agent for treating an inflammatory disease.

DETAILED DESCRIPTION OF THE INVENTION

Figures 1A, 1B:
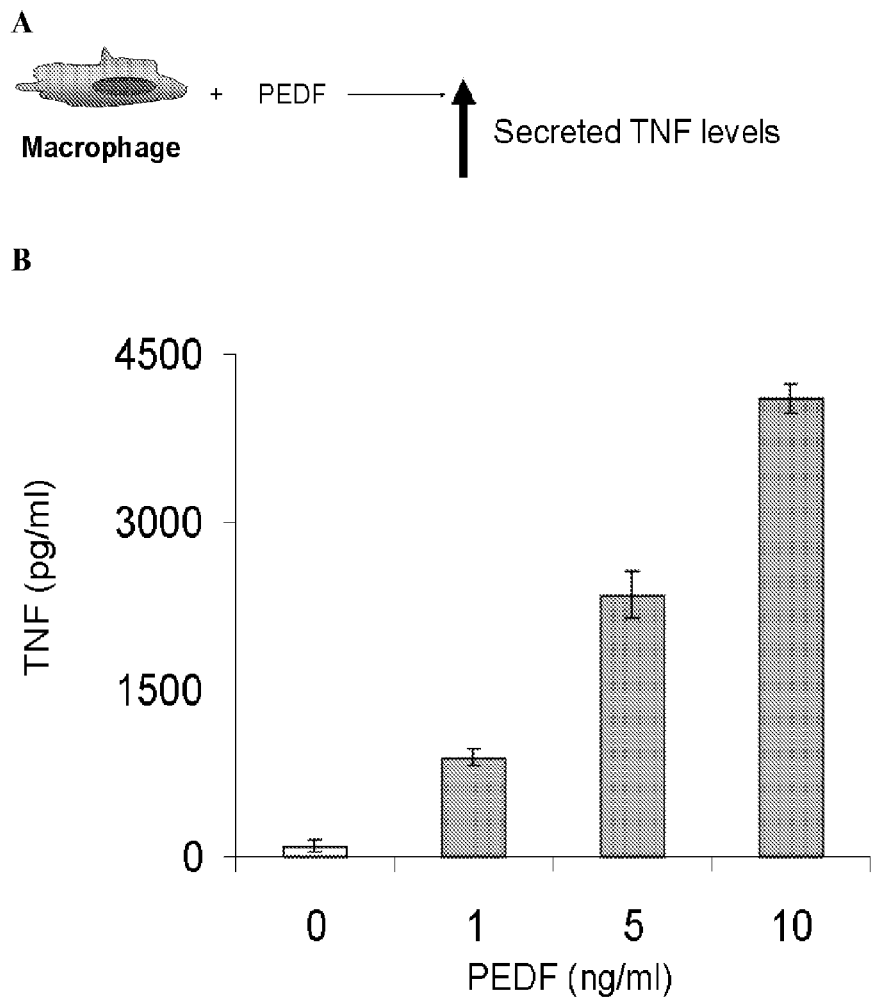
FIG. 1A-1B. (A) Pigment epithelium-derived factor (PEDF) induces tumor necrosis factor (TNF) production by macrophages. (B) TNF (pg/ml) induced by PEDF (ng/ml).

The present invention provides a method of treating an inflammatory disease in a subject, the method comprising administering to the subject a therapeutically effective amount of an agent that inhibits pigment epithelium-derived factor (PEDF).

The present invention provides the use of a PEDF inhibitor that inhibits PEDF for the treatment of an inflammatory disease in a subject.

Pigment epithelium-derived factor (PEDF) is also known as serpin F1 (SERPINF1) and is a noninhibitory serine protease inhibitor (a SERPIN family member). PEDF is a multifunctional secreted protein with anti-angiogenic, anti-tumorigenic and neurotrophic functions. Additionally, PEDF is a mediator released from adipocytes. PEDF is found in vertebrates. Pathways of PEDF may be upstream or downstream of PEDF. Upstream pathways comprise those RNA, DNA, protein or other biochemical events that result in the expression or activity of PEDF. Downstream pathways comprise those RNA, DNA, protein or other biochemical events whose expression or activity is dependent on the expression or activity of PEDF.

Treating an inflammatory disease means inhibiting or attenuating the clinical severity or disease progression of the inflammatory disease. A therapeutically effective amount is an amount that effects a clinically significant change in the symptoms, severity, or disease progression of the inflammatory disease. A therapeutically effective amount will depend on the subject, the subject's inflammatory disease, and the method of administration, among others. One of ordinary skill in the art can determine a therapeutically effective amount without undue experimentation.

In a preferred embodiment, the subject is obese or prediabetic. Obese and prediabetic subjects are more susceptible to cancers such as breast, esophageal, prostate, colon, endometrial or kidney cancers, obesity-related insulin resistance, polycystic ovary syndrome, metabolic syndrome, hypertension, cerebrovascular accident, myocardial infarction, congestive heart failure, cholecystitis, gout, osteoarthritis, Pickwickian syndrome, sleep apnea or atherosclerosis. For example, when the disease is a cancer, a therapeutically effective amount comprises an amount sufficient to retard the growth or metastasis of the cancer. In another example, when the inflammatory disease or condition is obesity-related insulin resistance or metabolic syndrome, a therapeutically effective amount comprises an amount sufficient to increase the subject's insulin sensitivity or attenuate or reverse the subject's risk factors for metabolic syndrome. In yet another example, when the inflammatory disease is osteoarthritis or atherosclerosis, a therapeutically effective amount comprises an amount sufficient to retard the disease progression or affect a clinically significant reduction in the severity of the subject's osteoarthritis or atherosclerosis.

In another preferred embodiment, the inflammatory disease or condition is endotoxemia or sepsis. In such a preferred embodiment, a therapeutically effective amount comprises an amount sufficient to reverse the subject's endotoxemia or sepsis, to retard the progression of the subject's endotoxemia or sepsis, or to affect a clinically significant reduction in the severity of the subject's endotoxemia or sepsis.

An agent inhibits PEDF if it limits the ability of PEDF, or a pathway thereof, to carry out its normal function, for example, by inhibiting an inflammatory effect of PEDF. The agent can inhibit PEDF, for example, by degrading, denaturing or binding to PEDF, by inhibiting the activity of PEDF, or by inhibiting the interaction between PEDF and a PEDF receptor, such as, for example, Adipose Triglyceride Lipase (ATGL) or Laminin Receptor (LR). Preferably, the agent binds to PEDF. The agent may be formulated in a pharmaceutical composition conveniently presented in unit dosage and may be prepared by any method known in the pharmaceutical art. Any pharmaceutically acceptable carrier must be compatible with the agent, and not deleterious to the subject. Examples of acceptable pharmaceutical carriers include caboxymethylcellulose, crystalline cellulose, glycerine, gum arabic, lactose, magnesium stearate, methyl cellulose, powders, saline, sodium alginate, sucrose, starch, talc and water, among others. Formulations of the pharmaceutical composition may conveniently be presented in unit dosage and may be prepared by any method known in the pharmaceutical art. For example, the agent may be brought into association with a carrier or diluent, as a suspension or solution. Optionally, one or more accessory ingredients, such as buffers, flavoring agents, surface active ingredients, and the like, may be added. The choice of carriers will depend on the method of administration. The agent or pharmaceutical composition thereof may be administered locally or systemically. For example, the agent or pharmaceutical composition thereof may be administered locally via injection into the site of the inflammatory disease. Systemic administration may include, for example, administration via parenteral, intravenous or oral means. The agent or pharmaceutical composition thereof would be useful for treating many different inflammatory diseases. The agent that inhibits PEDF is provided in amounts effective to treat the particular inflammatory disease. These amounts may be readily determined by one of ordinary skill in the art.

Treating an inflammatory disease in a subject may comprise administering a therapeutically effective amount of a PEDF inhibitor. The PEDF inhibitor can be any known in the art. Preferably, the PEDF inhibitor is an antibody. In the preferred embodiment, the antibody comprises a binding site that binds to PEDF or a protein in the PEDF pathway. The antibody can be produced by any method known in the art. Antibody encompasses whole antibodies and fragments thereof wherein the fragments specifically bind to PEDF or a protein in the PEDF pathway. An antibody or fragment thereof may bind to a PEDF receptor, inhibiting the interaction between the receptor and PEDF. For example, an antibody or fragment thereof may bind to the PEDF receptor LR (non-integrin 37/67-kDa laminin receptor) [17], or PEDF-R (TTS-2.2/independent phospholipase $A_2$ (PLA$_2$)ξ and mouse desnutrin/ATGL), also referred to as PNPLA2 (phospholipase $A_2$/nutrin/patatin-like phospholipase domain containing 2) [18]. The term antibody is further mean to encompass polyclonal antibodies and monoclonal antibodies. Antibodies may be produced by techniques well known to those skilled in the art. The antibody can be a human antibody or a non-human antibody such as goat antibody or a mouse antibody. Antibodies can be "humanized" by various well-known procedures involving standard recombinant DNA techniques. Antibodies can be recombinant and can be made by any method known in the art. The antibodies can then be purified by any method known in the art, for example, filtration, ion exchange chromatography, protein A/G affinity chromatography, or size exclusion chromatography.

Monoclonal antibodies are monospecific antibodies. Polyclonal antibodies are a combination of immunoglobulin molecules secreted against a specific antigen, each identifying a different epitope.

Inhibiting PEDF may comprise administering vagus nerve stimulation. Vagus nerve stimulation may be accomplished by a variety of techniques, among which is the use of an implanted stimulator to send electric impulses to the vagus nerve in the neck. For example, vagus nerve stimulation attenuates serum PEDF levels in endotoxemia.

Also provided is a screening method of identifying an agent for treating an inflammatory disease in a subject, the method comprising determining whether or not the agent inhibits pigment epithelium-derived factor (PEDF), wherein an agent that inhibits PEDF is identified as an agent for treating an inflammatory disease and an agent that does not inhibit PEDF is not identified as an agent for treating an inflammatory disease.

Figures 2A, 2B, 2C:
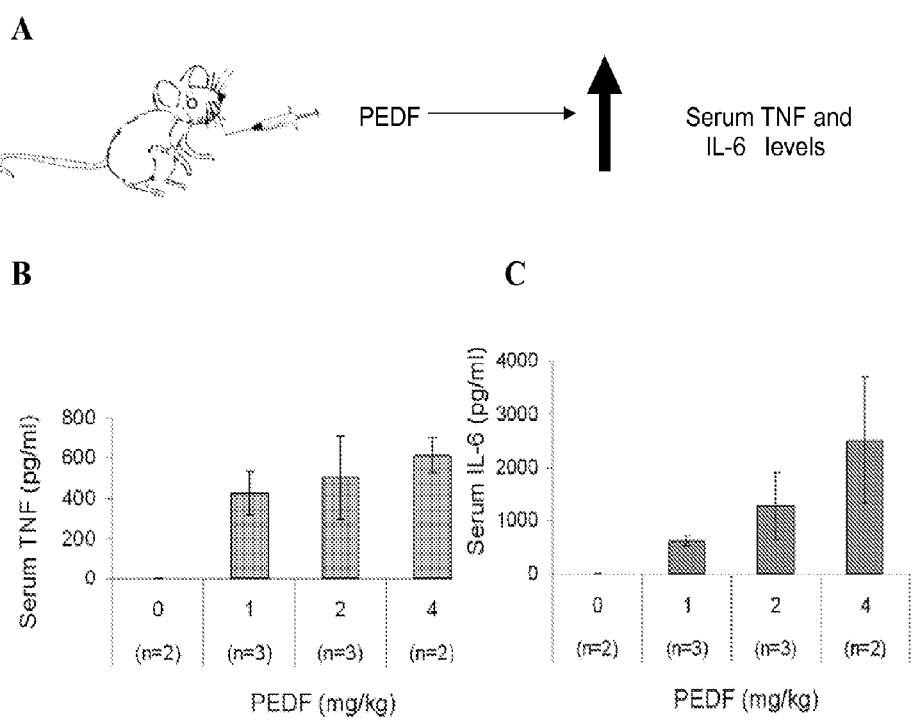
FIG. 2A-2C. (A) PEDF administration induces inflammatory phenotypes in mice. (B) Serum TNF induced by PEDF. (C) Serum interleukin 6 (IL-6) induced by PEDF.
Figures 3A, 3B, 3C:
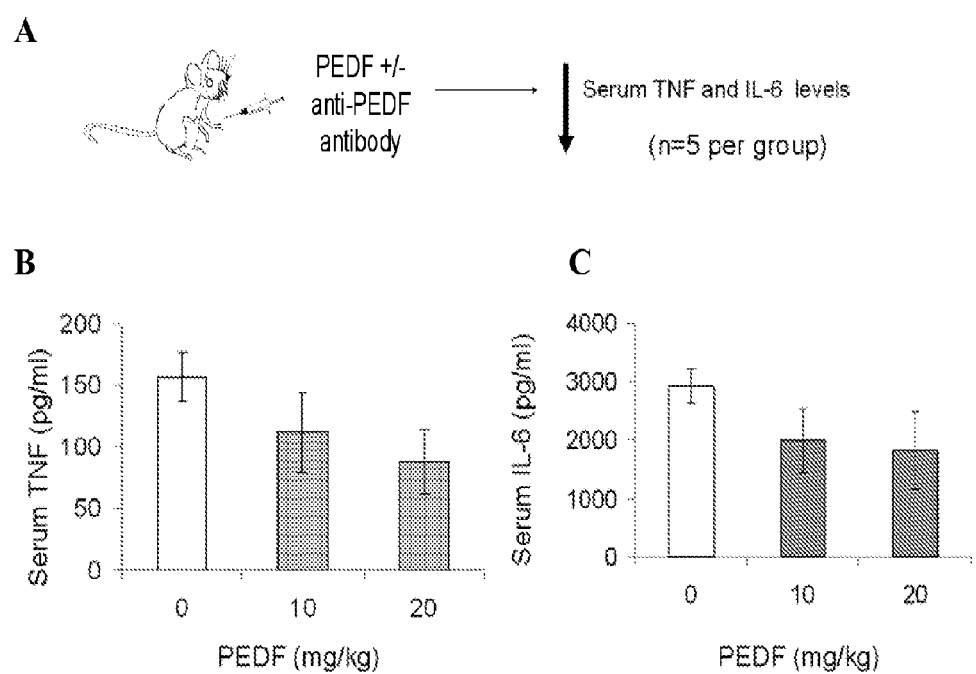
FIG. 3A-3C. (A) Neutralizing PEDF activity with anti-PEDF antibody attenuates PEDF-induced inflammation. (B) Serum TNF induced by PEDF is reduced by anti-PEDF antibody. (C) Serum IL-6 induced by PEDF is reduced by anti-PEDF antibody.
Figures 4A, 4B:
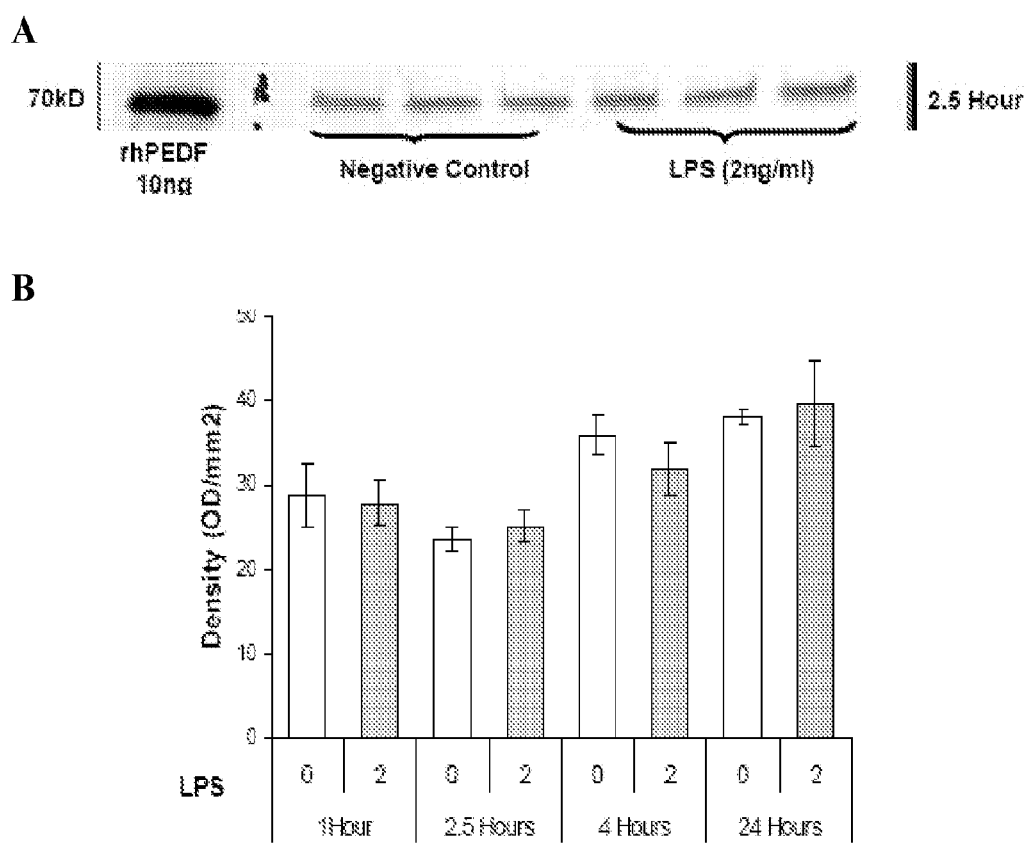
FIG. 4A-4B. Endotoxin does not induce increased PEDF production by macrophages. RAW cells were cultured with LPS (2 ng/ml). (A) Western blot analysis at 2.5 hours. (B) Cell culture supernatants were collected at different time points and analyzed for PEDF levels by western blot analysis.
Figure 5A:
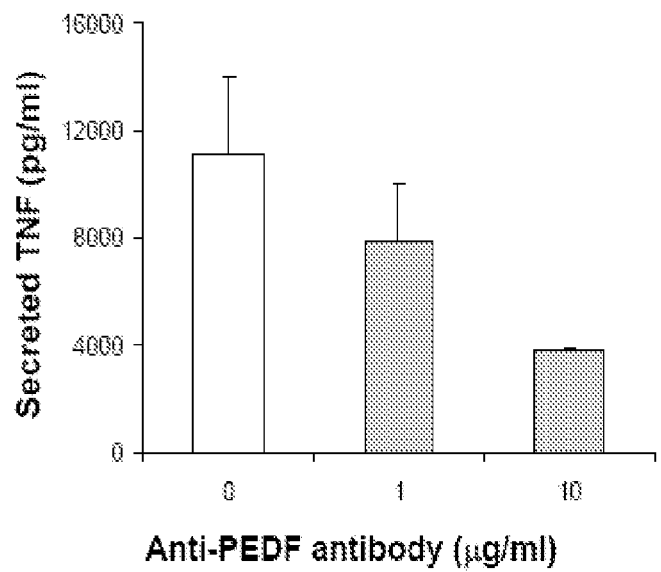
FIG. 5A-5B. (A) Anti-PEDF antibody attenuates endotoxin-induced TNF production by macrophages. RAW cells were cultured with anti-PEDF antibody and LPS. Cell culture supernatants were collected after 4 hours and TNF levels were determined by ELISA. (B) Anti-PEDF antibody attenuates serum TNF levels in murine endotoxemia. Anti-PEDF antibody was administered to mice 30 minutes prior to LPS administration. Serum TNF levels were quantitated after 90 minutes by ELISA.
Figure 5B:
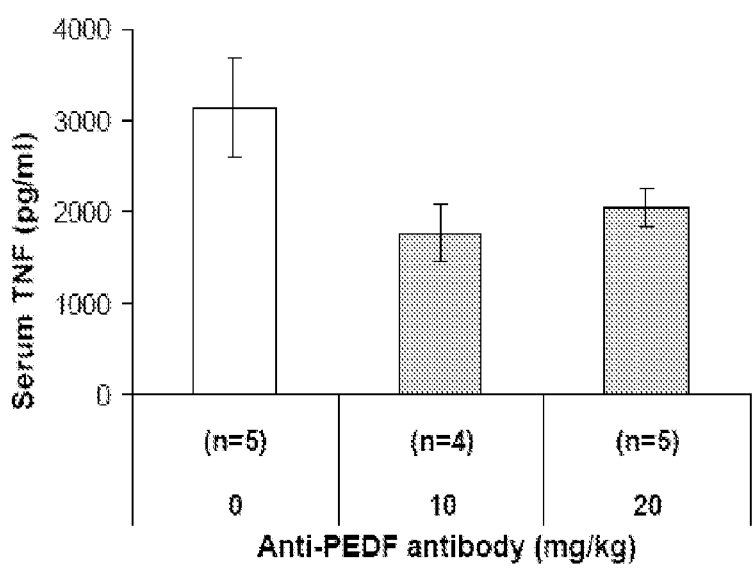
Figures 6A, 6B:
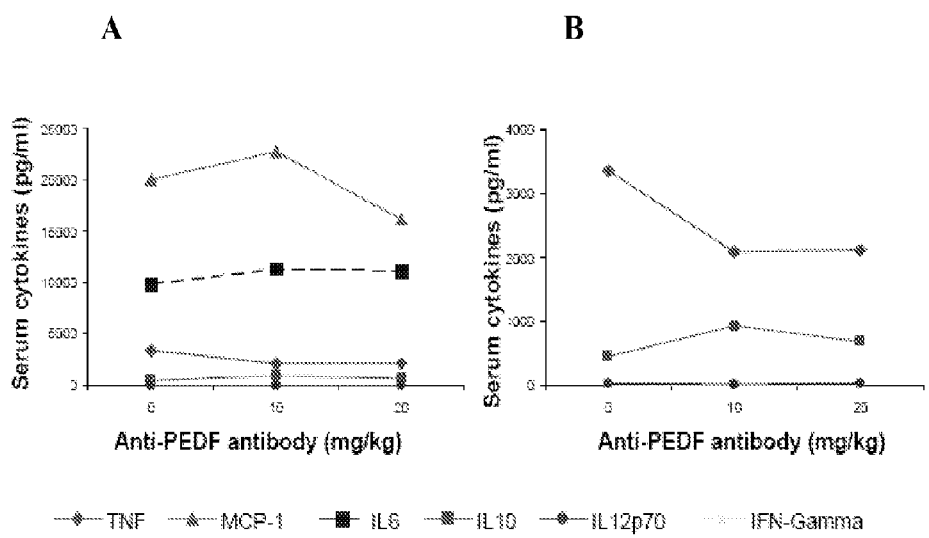
FIG. 6A-6B. Anti-PEDF antibody attenuates serum (A) TNF and (B) MCP1 levels in murine endotoxemia. Anti-PEDF antibody was administered to mice 30 minutes prior to LPS administration. Serum cytokine levels were quantitated after 90 minutes by cytokine bead analysis (BD Pharmingen).
Figure 7:
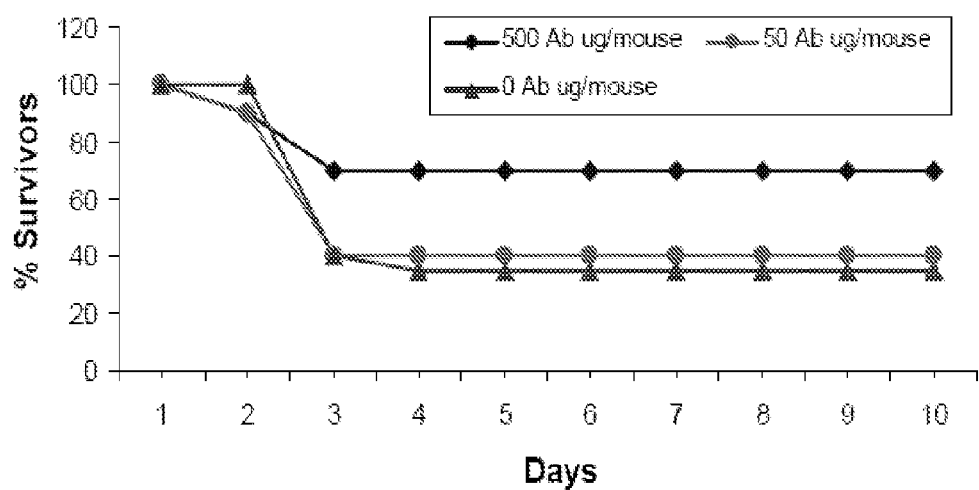
FIG. 7. Anti-PEDF antibody improves survival in murine endotoxemia. Anti-PEDF antibody was administered to mice 30 minutes prior to LPS administration. Survival was followed for 10 days (n=20 per group on day 1).
Figure 8:
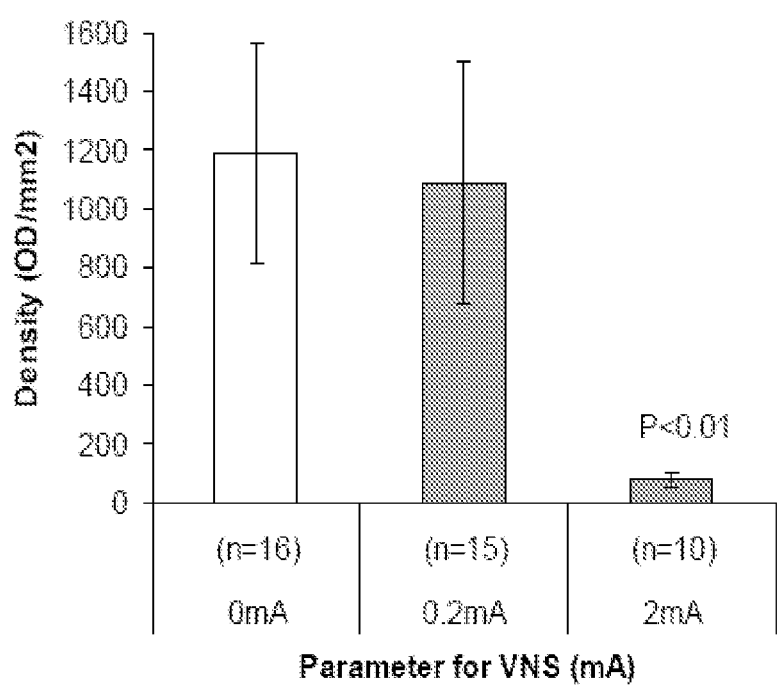
FIG. 8. Vagus nerve stimulation (VNS) attenuates serum PEDF levels in endotoxemia. Rats were subjected to electrical vagus nerve stimulation followed by endotoxemia. Serum PEDF levels were determined 90 minutes after by western blot analysis.
Figures 9A, 9B:
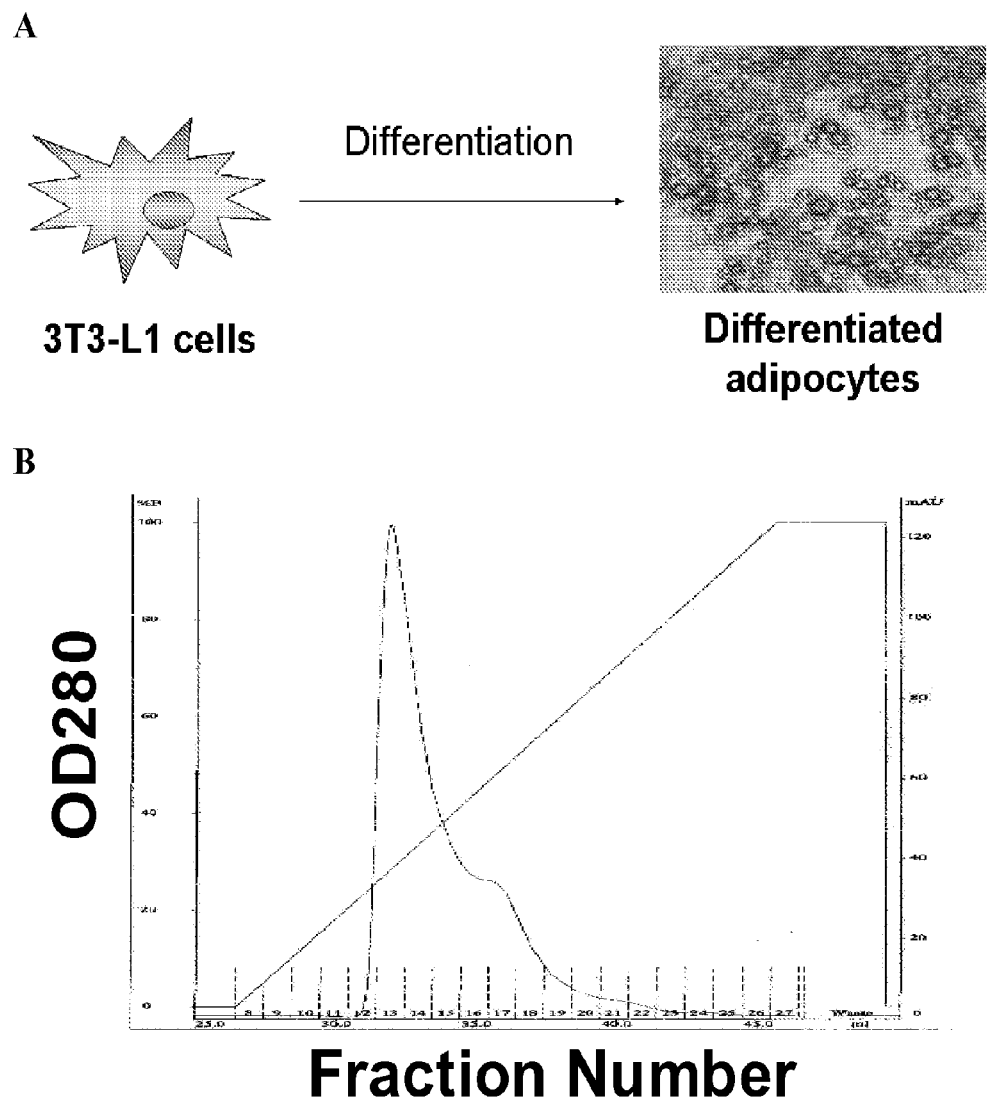
FIG. 9A-9B. Adipocyte conditioned medium (overnight, serum-free) was fractionated by ion exchange chromatography. (A) 3T3-L1 cells were differentiated into adipocytes (standard method). (B) Adipocyte conditioned medium fractionated by ion exchange chromatography.
Figures 10A, 10B:
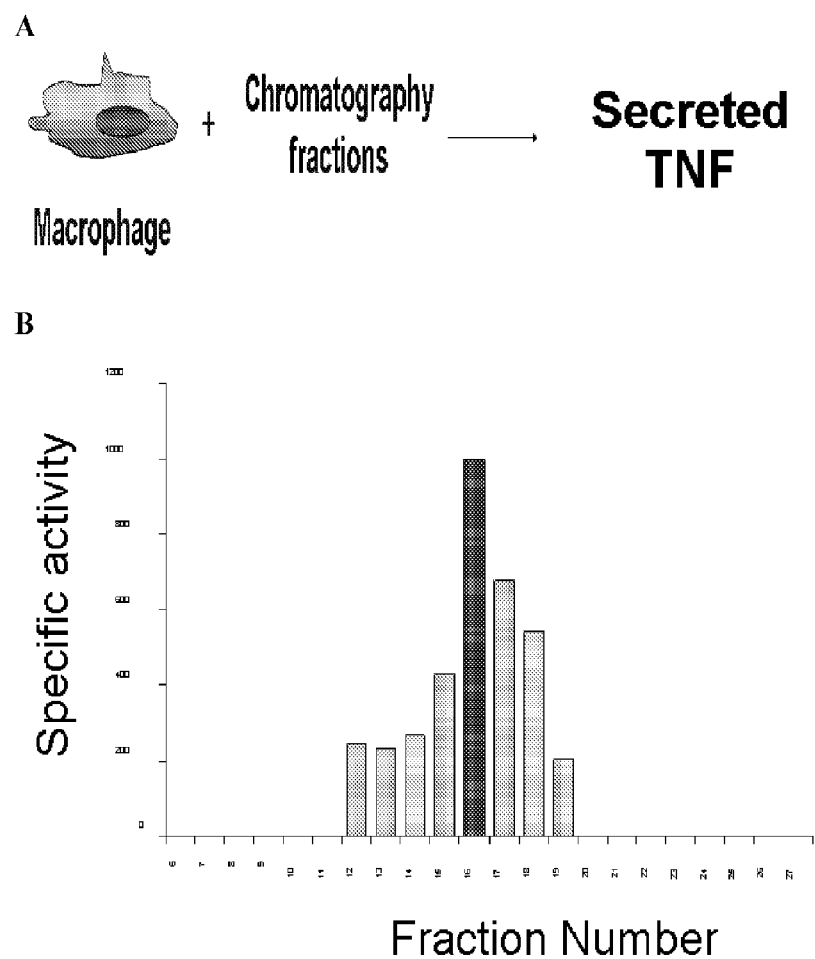
FIG. 10A-10B. PEDF was identified in adipocyte conditioned medium (overnight, serum-free) by mass spectrometry. (A) Macrophages were cultured with ion exchange chromatography fractions of adipocyte-conditioned medium and secreted TNF was analyzed by ELISA. (B) Specific activity of fractions for TNF induction was calculated. The unique band in the active fraction was analyzed by mass spectrometry and PEDF was identified as a macrophage stimulating adipocyte secretory factor.
Figures 11A, 11B:
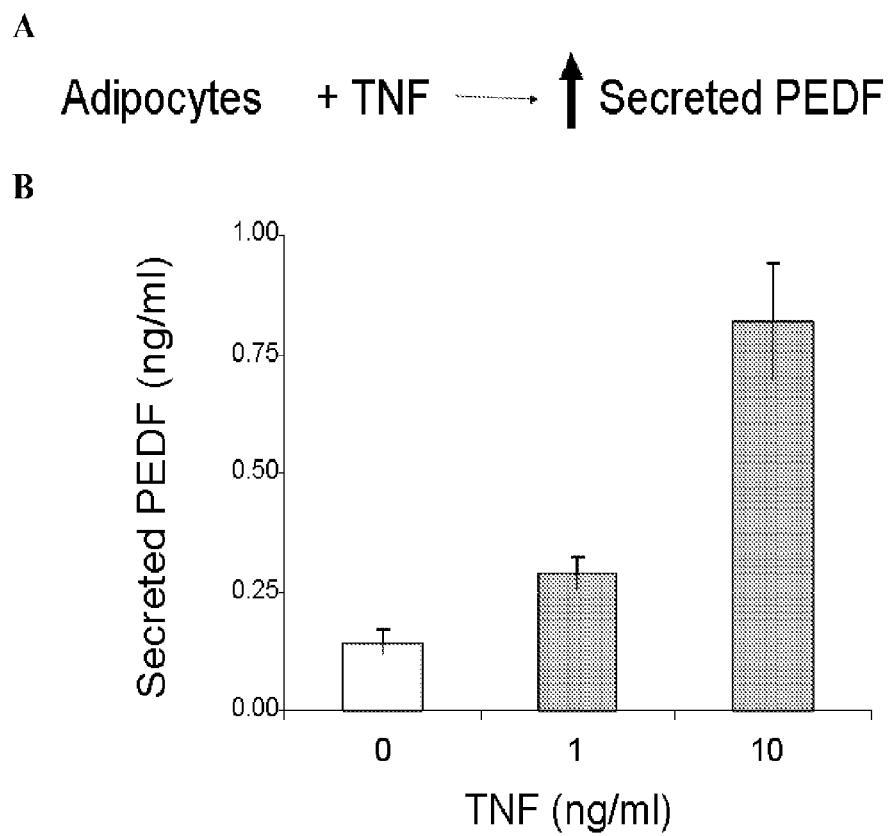
FIG. 11A-11B. TNF increases PEDF production by adipocytes. (A) TNF increases secreted PEDF by adipocytes. (B) Secreted PEDF induced by TNF.
Figure 12A:
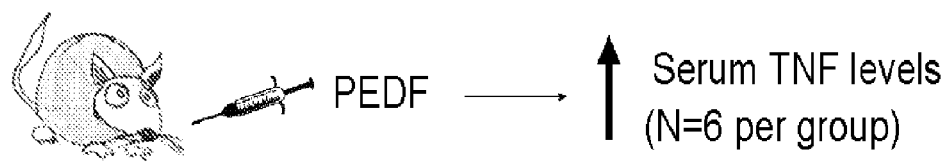
FIG. 12A-12B. (A) PEDF administration increases serum TNF levels in rats (n=6 per group). (B) Serum TNF induced by PEDF. Rats were treated with PEDF (2 mg/kg, i.v.). Blood was collected after ninety minutes for measurement of serum TNF (n=6 per group). Serum TNF ninety minutes after PEDF injection. P<0.05.
Figure 12B:
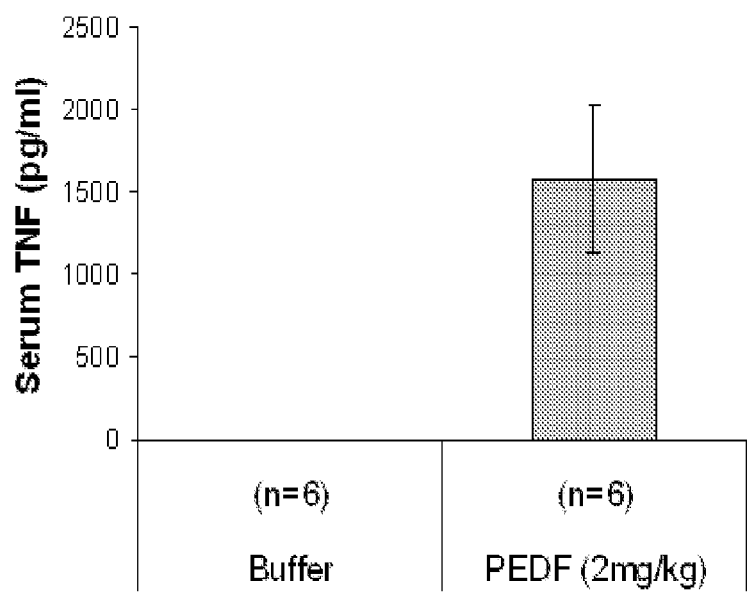
Figure 13A:
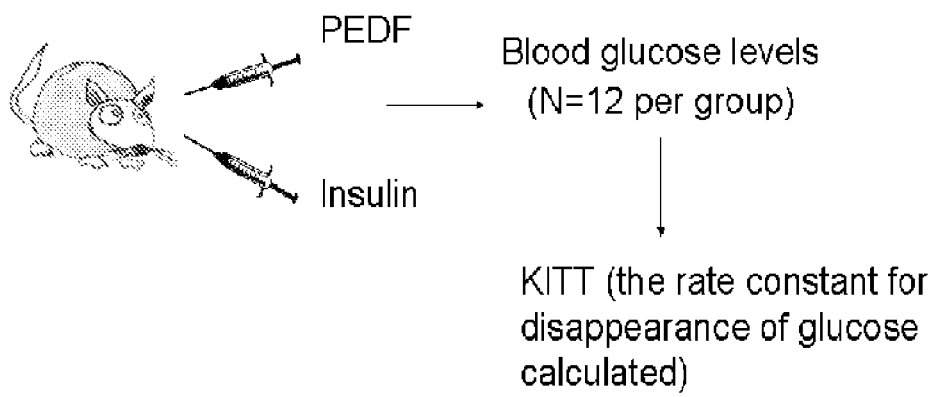
FIG. 13A-13B. PEDF administration induces insulin resistance. (A) PEDF administration increases blood glucose levels. KITT (rate constant for disappearance of glucose) decreases. n=12 per group. (B) KITT versus PEDF. Rats were treated with PEDF (2 mg/kg, i.v.). Blood was collected after ninety minutes and an insulin tolerance test was performed. KITT is inversely related to insulin resistance.
Figure 13B:
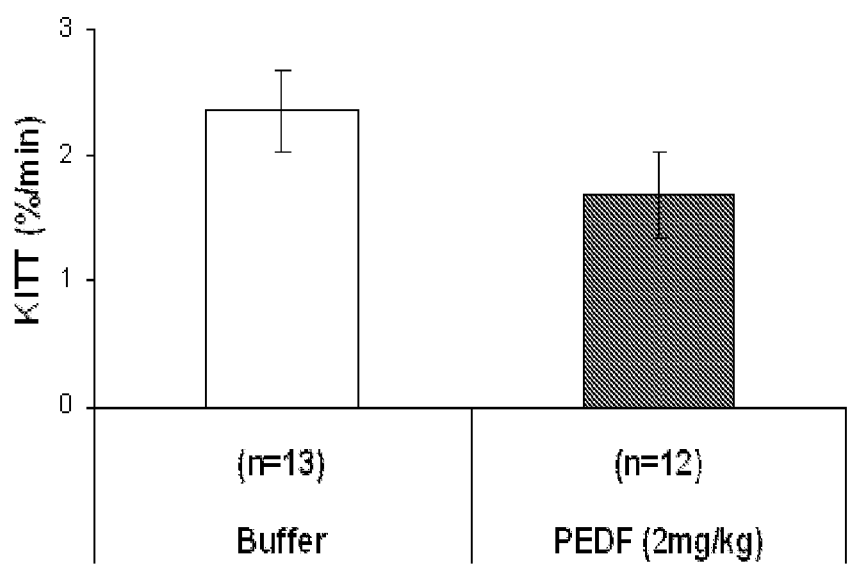
Figure 14:
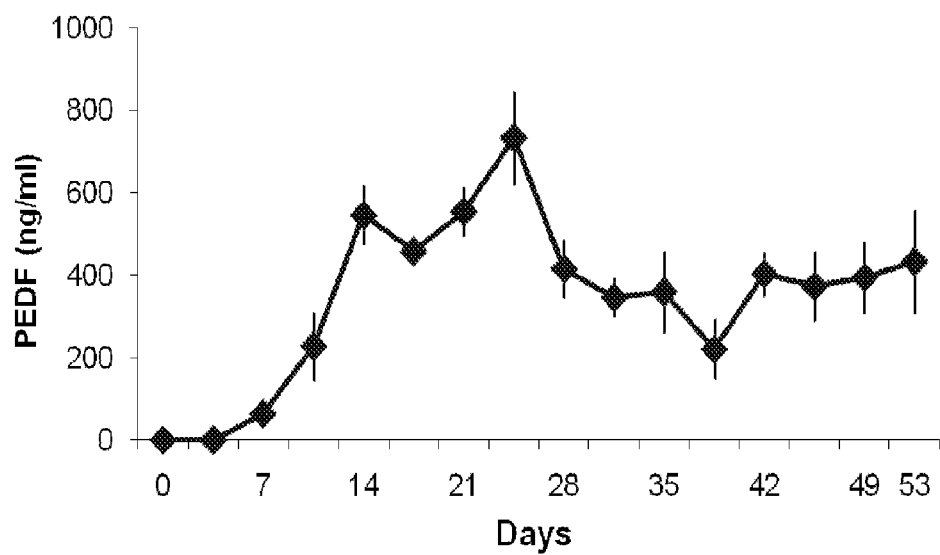
FIG. 14. PEDF is secreted by differentiated adipocytes. 3T3-L1 cells were differentiated into adipocytes in the presence of insulin and dexamethasone. Levels of PEDF were quantitated in the supernatants at shown time points by ELISA.
Figure 15:
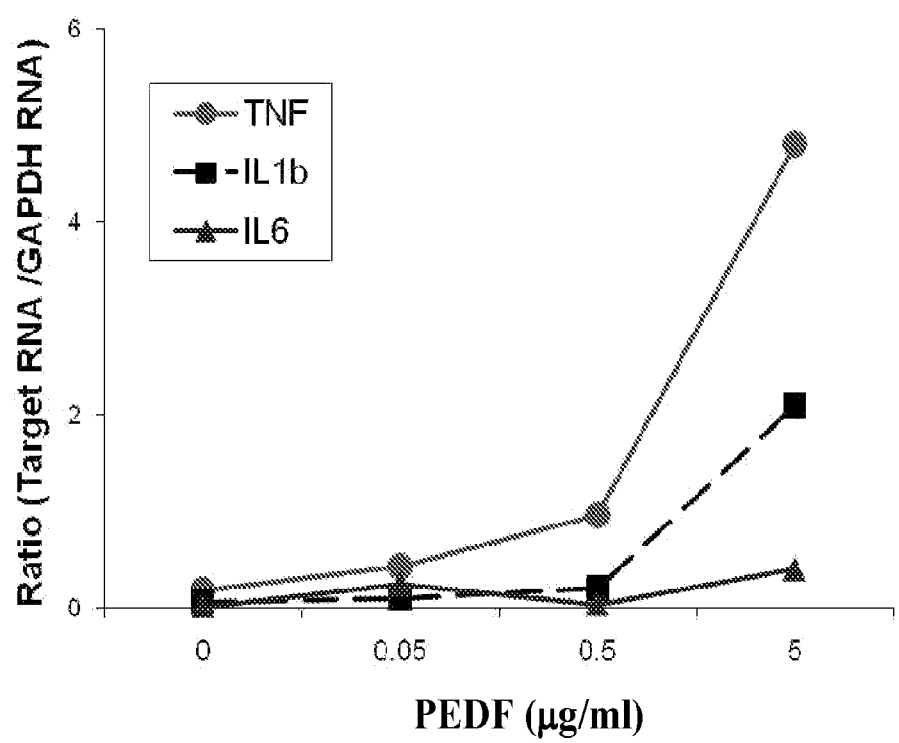
FIG. 15. PEDF induces increased expression of inflammatory cytokines by macrophages. Murine macrophage RAW 264 cells were cultured for 1 hr with different concentrations of recombinant PEDF. Levels of cytokine mRNA were quantitated by quantitative PCR.
Figure 16:
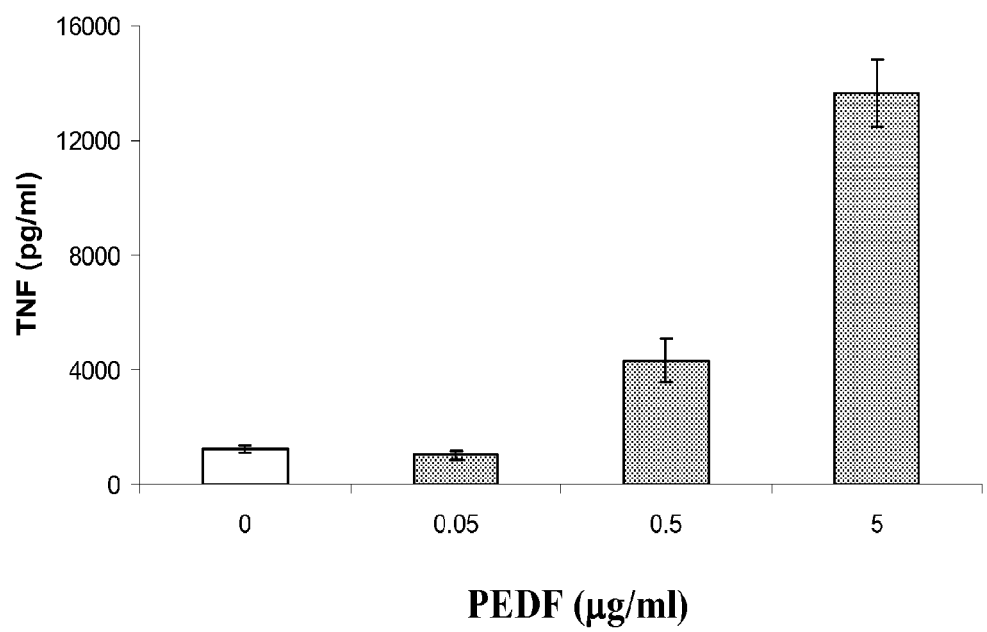
FIG. 16. PEDF induces concentration dependent increase in TNF secretion by macrophages. Murine macrophage RAW 264 cells were cultured for 2.5 hr with increasing concentrations of recombinant PEDF. TNF levels were analyzed in the supernatant by ELISA.
Figure 17A:
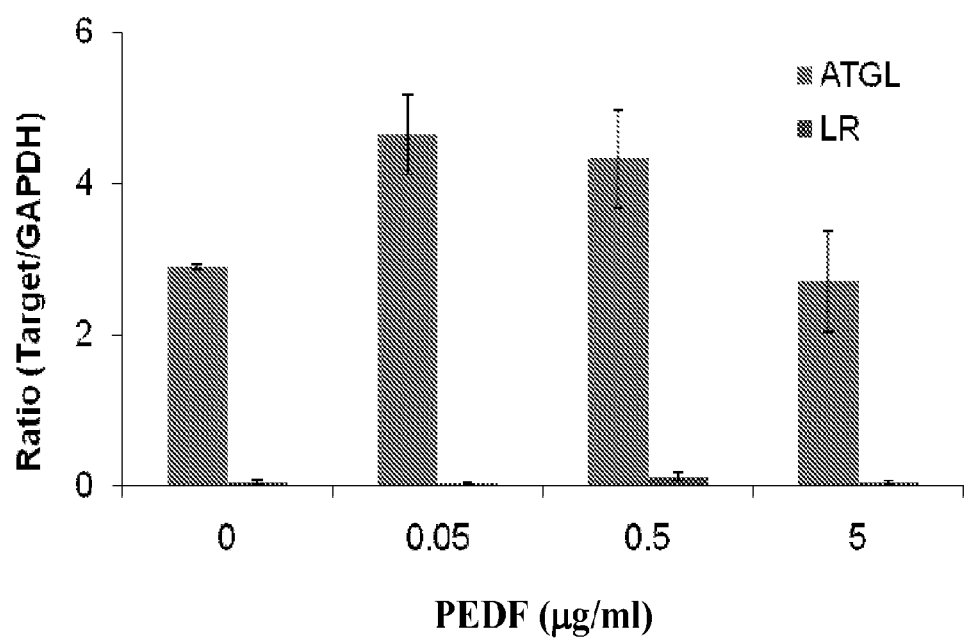
FIG. 17A-17B. Macrophages constitutively express PEDF receptor ATGL (Adipose Triglyceride Lipase). A. Expression of PEDF receptors (ATGL and LR, Laminin receptor) was studied by quantitative PCR in macrophages. B. ATGL expression was studied in total cell lysate from macrophages and adipocytes by western blotting.
Figure 17B:
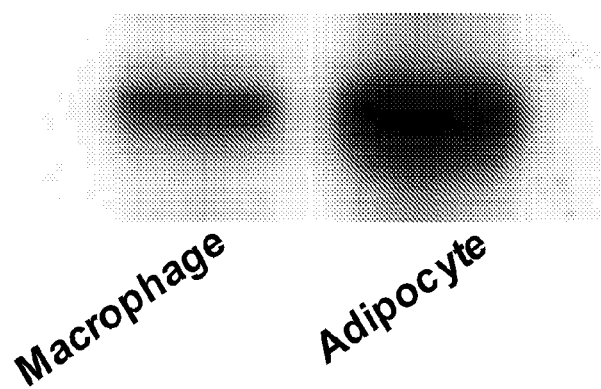
Figure 18A:
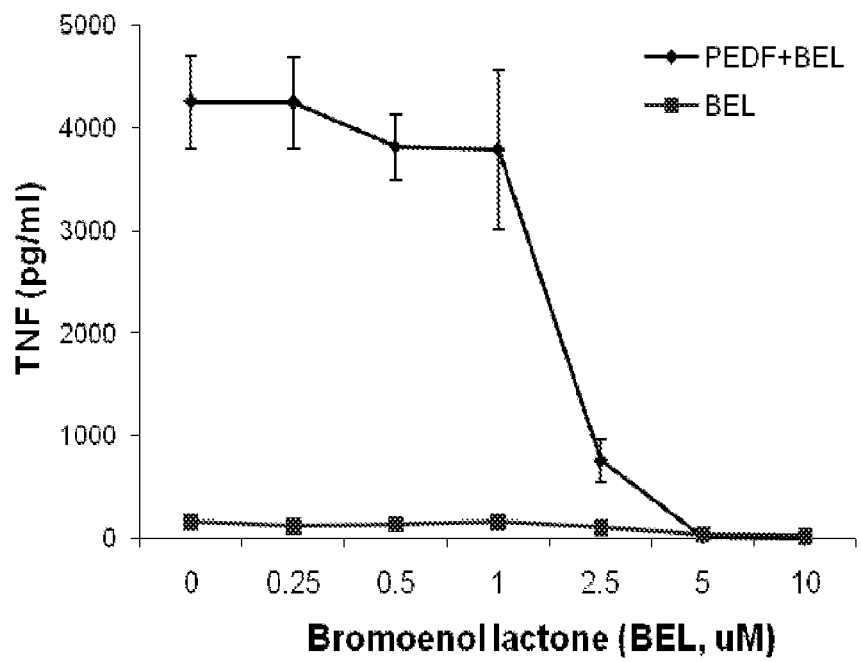
FIG. 18A-18C. ATGL inhibitors bromoenol lactone (BEL) (A), methyl arachidonyl fluorophosphonate (MAFP) (B) and arachidonyl trifluoromethyl ketone (AACOCF3) (C) attenuate PEDF-induced TNF release by macrophages. RAW macrophages were cultured with PEDF in the presence of increasing concentrations of ATGL inhibitor. Levels of TNF were analyzed in the cell supernatant after 2.5 hr by ELISA.
Figure 18B:
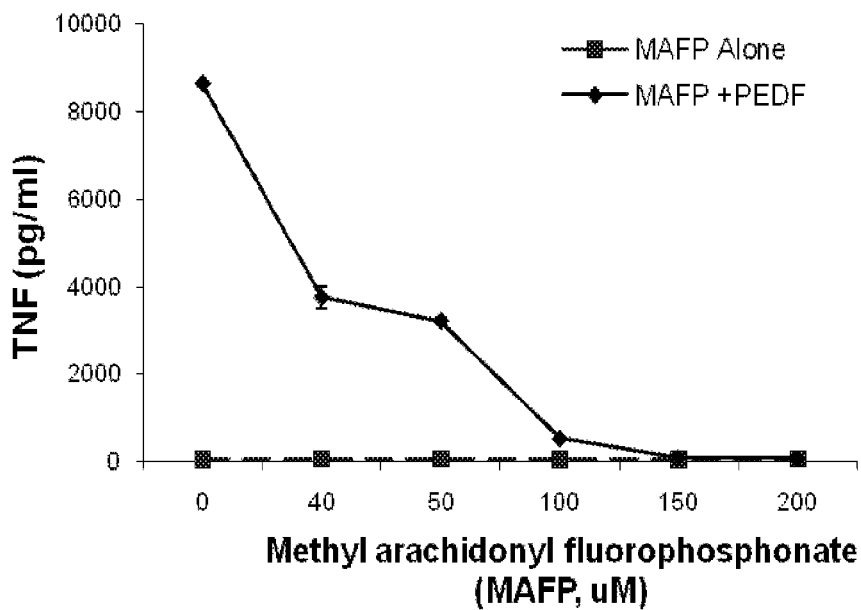
Figure 18C:
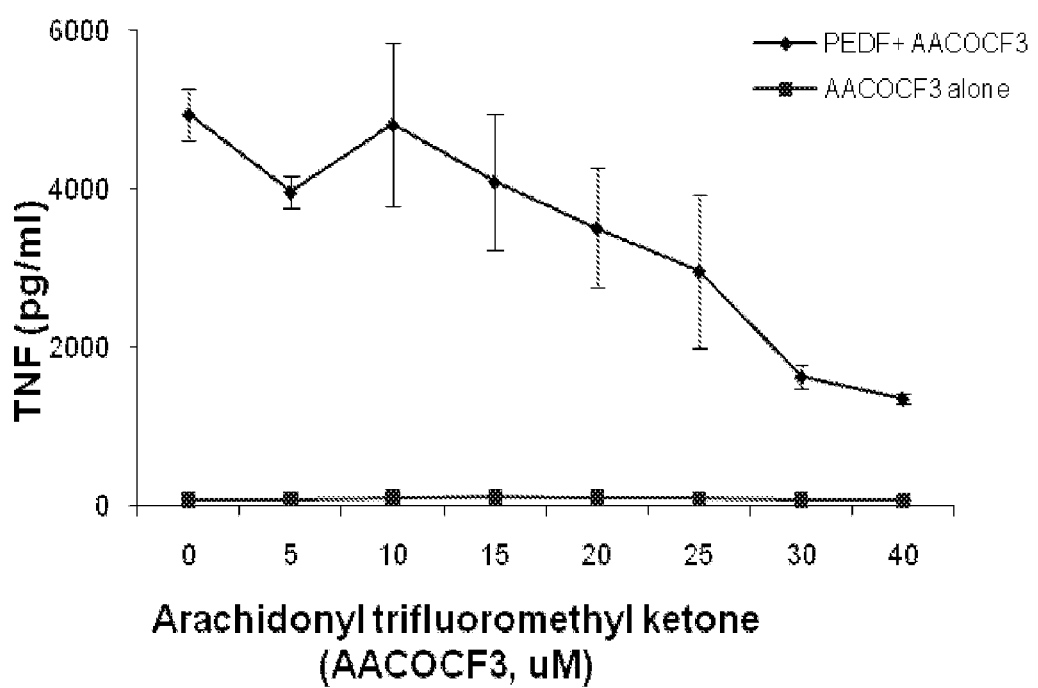
Figures 19A, 19B:
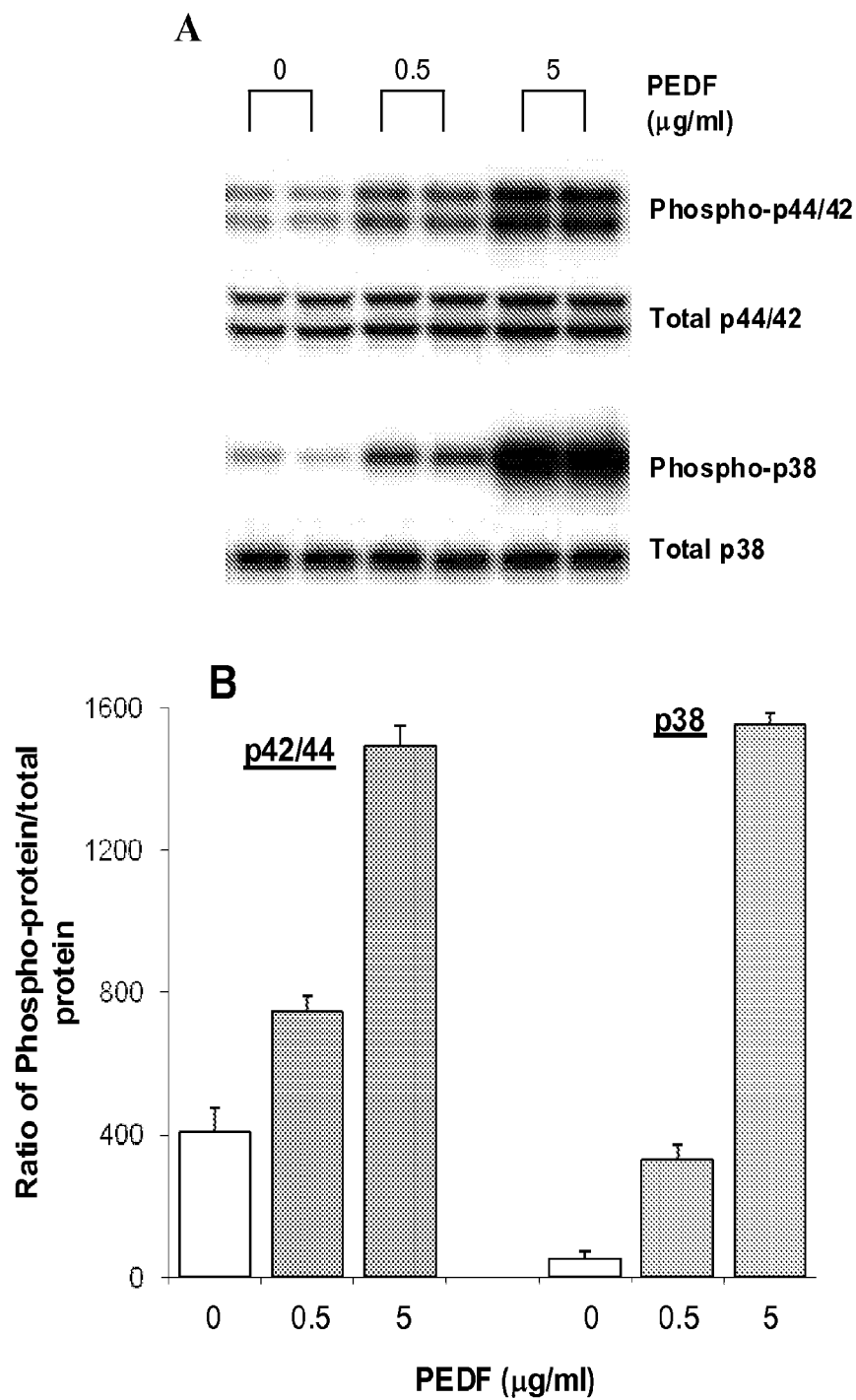
FIG. 19A-19B. PEDF induces activation of p38 MAP kinase and ERK1/2 kinase in macrophages in concentration dependent manner. Expression of phosphorylated and total protein (p38 and p44/42) in PEDF stimulated RAW cells was analyzed by western blot analysis. A. Western blot analysis B. Densitometric analysis of phosphorylated kinases.
Figure 20:
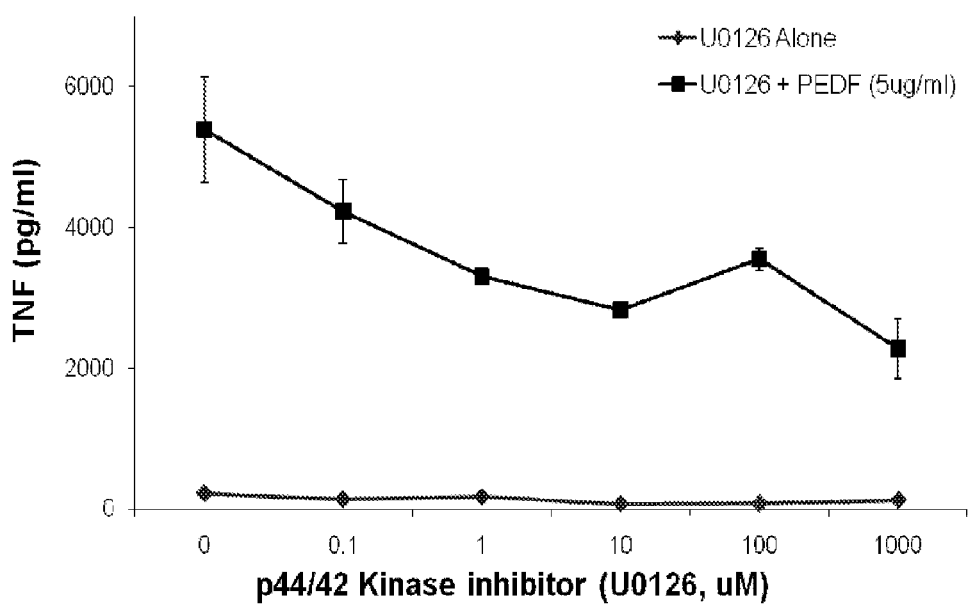
FIG. 20. Inhibition of p44/42 MAP kinase attenuates PEDF-induced TNF release by macrophages. RAW macrophages were cultured with PEDF in the presence of increasing concentrations of p44/42 MAP kinase inhibitor. Levels of TNF were analyzed in the cell supernatant after 2.5 hr by ELISA.
Figure 21:
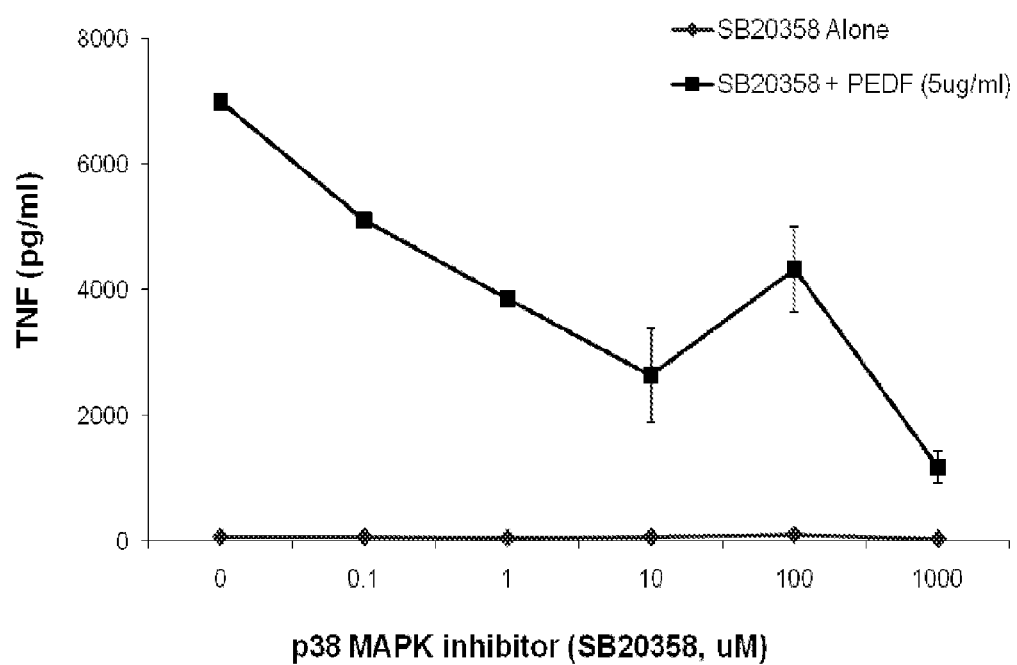
FIG. 21. Inhibition of p38 MAP kinase attenuates PEDF-induced TNF release by macrophages. RAW macrophages were cultured with PEDF in the presence of increasing concentrations of p38 MAP kinase inhibitor. Levels of TNF were analyzed in the cell supernatant after 2.5 hr by ELISA.

Pigment epithelium-derived factor (PEDF) induces production of, among other pro-inflammatory mediators of the inflammatory cytokine cascade, tumor necrosis factor (TNF), Interleukin-1b (IL-1b) and Interleukin-6 (IL-6) by macrophages (e.g., FIGS. 1, 15 and 16), induces activation of p38 MAP kinase and ERK1/2 kinase in macrophages (e.g., FIG. 19), increases serum TNF and IL-6 levels (e.g., FIG. 2), and induces insulin resistance (e.g., FIG. 13). An assay for identifying an agent for treating an inflammatory disease could, for example, test whether or not the agent inhibits PEDF's effect on any one or more of these parameters. Thus, for example, in one embodiment, the method can comprise determining whether or not the agent inhibits PEDF-induced production of TNF, IL-1b or IL-6 by macrophages, wherein an agent that inhibits PEDF-induced production of TNF, IL-1b or IL-6 by macrophages is identified as an inhibitor of PEDF and an agent that does not inhibit PEDF-induced production of TNF, IL-1b or IL-6 by macrophages is not identified as an inhibitor of PEDF. Similarly, for example, the method can comprise determining whether or not the agent inhibits PEDF-induced activation of p38 MAP kinase or ERK1/2 kinase in macrophages, wherein an agent that inhibits PEDF-induced activation of p38 MAP kinase or ERK1/2 kinase in macrophages is identified as an inhibitor of PEDF and an agent that does not inhibit PEDF-induced activation of p38 MAP kinase or ERK1/2 kinase in macrophages is not identified as an inhibitor of PEDF. In another embodiment, the method can comprise determining whether or not the agent inhibits PEDF-induced increase in serum level of TNF or IL-6 or IL-1b, wherein an agent that inhibits PEDF-induced increase in serum level of TNF or IL-6 or IL-1b is identified as an inhibitor of PEDF and an agent that does not inhibit PEDF-induced increase in serum level of TNF or IL-6 or IL-1b is not identified as an inhibitor of PEDF.

The invention further provides an agent for treating an inflammatory disease identified by any of the screening methods disclosed herein.

The inflammatory disease may be any disease whose biological mechanism is linked to acute or chronic inflammation. For example, the inflammatory disease may be endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea or atherosclerosis.

The subject may be any vertebrate. In a preferred embodiment, the subject is a mammal. For example, the subject may be a rodent or a human.

In a preferred embodiment, PEDF is human PEDF having the amino acid sequence set forth below (ACCESSION NO. P36955) (SEQ ID NO:1):

```
  1 mqalvlllci gallghsscq npasppeegs pdpdstgalv eeedpffkvp vnklaaaysn
 61 fgydlyrvrs stspttnvll splsvatals alslgaeqrt esiihralyy dlisspdihg
121 tykelldtvt apqknlksas rivfekklri kssfvaplek sygtrprvlt gnprldlqei
181 nnwvqaqmkg klarstkeip deisilllgv ahfkgqwvtk fdsrktsled fyldeertvr
241 vpmmsdpkav lrygldsdls ckiaqlpltg smsiifflpl kvtqnitlie esltsefihd
301 idrelktvqa vltvpklkls yegevtkslq emklqslfds pdfskitgkp ikltqvehra
361 gfewnedgag ttpspglqpa hltfpldyhl nqpfifvlrd tdtgallfig kildprgp
``` sion, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, coeliac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In a preferred embodiment, the inflammatory disease or condition is endotoxemia or sepsis. In another preferred embodiment, the subject is prediabetic or obese. Subjects who are obese or prediabetic are more susceptible to certain inflammatory diseases or conditions. In such a preferred embodiment, the inflammatory disease may be cancers such as breast, esophageal, prostate, colon, endometrial or kidney cancers, obesity-related insulin resistance, polycystic ovary syndrome, metabolic syndrome, hypertension, cerebrovascular accident, myocardial infarction, congestive heart failure, cholecystitis, gout, osteoarthritis, Pickwickian syndrome, sleep apnea or atherosclerosis.

REFERENCES

1. Tracey, K. J. (2002). The inflammatory reflex. Nature 420, 853-859.
2. Ulloa, L. & Tracey, K. J. (2005). The 'cytokine profile': A code for sepsis. Trends in Molecular Medicine 11(2), 56-63.
3. Parrish, W. R., Gallowitsch-Puerta, M., Czura, C. J., & Tracey, K. J. (In Press). Experimental therapeutic strategies for severe sepsis: Mediators and mechanisms. Annals of the New York Academy of Sciences.
4. Tracey, K. J. (2005). Fatal Sequence: The Killer Within. Dana Press, distributed by The University of Chicago.
5. Marshall, J. C., Cook, D. J., Christou, N. V., Bernard, G. R., Sprung, C. L., & Sibbald, W. J. (1995). Multiple organ dysfunction score: a reliable descriptor of a complex clinical outcome. Critical Care Medicine 23, 1638-1652.
6. Riedemann, N. C., Guo, R. F., & Ward, P. A. (2003). Novel strategies for the treatment of sepsis. Nature Medicine 9, 517-524.
7. Tracey, K. J., Fong, Y., Hesse, D. G., Manogue, K. R., Lee, A. T., Kuo, G. C., Lowry, S. F., & Cerami, A. (1987). Anti-cachectin/TNF monoclonal antibodies prevent septic shock during lethal bacteraemia. Nature 330, 662-664.
8. Tracey, K. J., Beutler, B., Lowry, S. F., Merryweather, J., Wolpe, S., Milsark, I. W., Hariri, R. J., Fahey, T. J., Zantella, A., Albert, J. D., et al. (1986). Shock and tissue injury induced by recombinant human cachectin. Science 234, 470-474.
9. Wang, H., Bloom, O., Zhang, M., Vishnubhakat, J. M., Ombrellino, M., Che, J., Frazier, A., Yang, H., Ivanova, S., Borovikova, L., Manogue, K. R., Faist, E., Abraham, E., Andersson, J., Andersson, U., Molina, P. E., Abumrad, N. N., Sama, A., & Tracey, K. J. (1999). HMG-1 as a late mediator of endotoxin lethality in mice. Science 285, 248-251.
10. Tracey, K. J. & Abraham, E. (1999). From mouse to man: Or what have we learned about cytokine-based anti-inflammatory therapies? Shock 11, 224-225.
11. Andersson, U., Wang, H., Palmblad, K., Aveberger, A. C., Bloom, O., Erlandsson-Harris, H., Janson, A., Kokkola, R., Zhang, M., Yang, H., & Tracey, K. J. (2000). High mobility group 1 protein (HMG-1) stimulates proinflammatory cytokine synthesis in human monocytes. The Journal of Experimental Medicine 192, 565-570.
12. Ferrara, J. L., Abhyankar, S., & Gilliland, D. G. (1993). Cytokine storm of graft-versus-host disease: A critical effector role for interleukin-1. Transplantation Proceedings 25(1 Pt 2), 1216-1217.
13. Giroir, B. P. (1993). Mediators of septic shock: New approaches for interrupting the endogenous inflammatory cascade. Critical Care Medicine 21(5), 780-789.
14. Ulloa, L., Ochani, M., Yang, H., Tanovic, M., Halperin, D., Yang, R., Czura, C. J., Fink, M. P., & Tracey, K. J. (2002). Ethyl pyruvate prevents lethality in mice with established lethal sepsis and systemic inflammation. Proceedings of the National Academy of Sciences of the United States of America 99, 12351-12356.
15. Wang, H., Yang, H., Czura, C. J., Sama, A. E., & Tracey, K. J. (2001). HMGB1 as a late mediator of lethal systemic inflammation. American Journal of Respiratory and Critical Care Medicine 164, 1768-1773.
16. Czura, C. J., Yang, H., & Tracey, K. J. (2003). High mobility group box-1 as a therapeutic target downstream of tumor necrosis factor. The Journal of Infectious Diseases 187, S391-S396.
17. Bernard, A., Gao-Li, J., Franco, C. A., Bouceba, T., Huet, A., & Li, Z. (2009). Laminin receptor involvement in the anti-angiogenic activity of pigment epithelium-derived factor. The Journal of Biological Chemistry 284, 10480-10490.
18. Notari, L., Baladron, V., Aroca-Aguilar, J. D., Balko, N., Heredia, R., Meyer, C., Notario, P. M., Saravanamuthu, S., Nueda, M. L., Sanchez-Sanchez, F., Escribano, J., Laborda, J., & Becerra, S. P. (2006). Identification of a lipase-linked cell membrane receptor for pigment epithelium-derived factor. Journal of Biological Chemistry 281, 38022-38037.

What is claimed is:

1. A method of treating a disease or disorder in a subject, the method comprising administering to the subject a therapeutically effective amount of an antibody that binds to and inhibits pigment epithelium-derived factor (PEDF), wherein the disease or disorder is selected from the group consisting of endotoxemia, sepsis, septicemia, and endotoxic shock.

2. The method of claim 1, wherein the disease or disorder is endotoxemia.

3. The method of claim 1, wherein the disease or disorder is sepsis.

4. The method of claim 1, wherein the disease or disorder is septicemia.

5. The method of claim 1, wherein the disease or disorder is endotoxic shock.

6. The method of claim 1, wherein the antibody is a monoclonal antibody.

7. The method of claim 1, wherein the antibody is a humanized or human antibody.

8. The method of claim 1, wherein the subject is a mammal.

9. The method of claim 8, wherein the subject is a human.

* * * * *

SEQUENCE LISTING

```
<160> NUMBER OF SEQ ID NOS: 1

<210> SEQ ID NO 1
<211> LENGTH: 418
<212> TYPE: PRT
<213> ORGANISM: Homo sapiens

<400> SEQUENCE: 1

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240
```

-continued

```
Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```